(12) United States Patent
Dang et al.

(10) Patent No.: US 6,465,653 B2
(45) Date of Patent: Oct. 15, 2002

(54) NONCATALYZED SYNTHESIS OF 4-HYDROXYQUINOLINES AND/OR TAUTOMERS THEREOF

(75) Inventors: Taun-Phat Dang, Lyons; Alain Roustan, Saint Genis Laval, both of (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/814,940

(22) Filed: Mar. 23, 2001

(65) Prior Publication Data

US 2002/0007067 A1 Jan. 17, 2002

Related U.S. Application Data

(63) Continuation of application No. PCT/FR99/02263, filed on Sep. 23, 1999.

(51) Int. Cl.$^7$ .................... C07D 215/18; C07D 217/16
(52) U.S. Cl. ........................ 546/152; 546/141
(58) Field of Search ................................ 546/152, 141

(56) References Cited

U.S. PATENT DOCUMENTS

| | | | |
|---|---|---|---|
| 2,504,875 A | | 4/1950 | Price et al. |
| 3,910,898 A | | 10/1975 | Allais et al. |
| 3,910,922 A | | 10/1975 | Allais et al. |
| 4,380,632 A | | 4/1983 | Steffen |
| 4,390,541 A | * | 6/1983 | Goldworthy et al. ....... 546/153 |
| 5,731,440 A | * | 3/1998 | Yoshizawa et al. ......... 546/156 |

FOREIGN PATENT DOCUMENTS

| | | |
|---|---|---|
| EP | 0 055 068 A1 | 6/1982 |
| WO | WO 98/33774 A1 | 8/1998 |

* cited by examiner

*Primary Examiner*—Alan L. Rotman
*Assistant Examiner*—Rita Desai
(74) *Attorney, Agent, or Firm*—Burns, Doane, Swecker & Mathis, L.L.P.

(57) ABSTRACT

The 4-hydroxyquinoline compounds and/or tautomers thereof, notably 4-hydroxy-5,7-dichchloroquinoline, are synthesized in very high yields by hydrolyzing/decarboxylating a 4-hydroxyquinolinecarboxylic acid ester in the presence of water, whether in liquid or vapor state, but in the absence of any catalyst for such reaction(s).

20 Claims, No Drawings

NONCATALYZED SYNTHESIS OF 4-HYDROXYQUINOLINES AND/OR TAUTOMERS THEREOF

CROSS-REFERENCE TO PRIORITY/PCT APPLICATIONS

This application claims priority under 35 U.S.C. § 119 of FR-98/12163, filed Sep. 29, 1998, and is a continuation of PCT/FR-99/02263, filed Sep. 23, 1999 and designating the United States (published in French on Apr. 6, 2000 as WO 00/18739), both hereby expressly incorporated by reference.

BACKGROUND OF THE INVENTION

1. Technical Field of the Invention

The present invention relates to a novel process for the noncatalytic preparation of the 4-hydroxyquinolines and/or the tautomeric forms thereof.

This invention more especially relates to the preparation of 5,7-dichloro-4-hydroxyquinoline and/or tautomers thereof.

2. Description of the Prior Art 5,7-dichloro-4-hydroxyquinoline (DCHQ) is a known and valuable intermediate in the plant protection field.

The industrial scale preparation of such a product presents a variety of problems, and existing processes are in serious need of refining.

U.S. Pat. No. 5,731,440 and C. C. Price et al. (Organic Synthesis, 3, p. 272) describes the preparation of 4-hydroxyquinolines via a process entailing decarboxylation of 4-hydroxy-3-quinolinecarboxylic acids that have been obtained by alkaline or acid hydrolysis of the corresponding esters.

A process of that type has also been described in WO-A-98/33774, comprising hydrolyzing the ester function followed by acidification, separating the 4-hydroxy-3-quinolinecarboxylic acid obtained by filtration, then followed by decarboxylation carried out at a temperature from 190° C. to 240° C., preferably from 210° C. to 230° C.

One marked drawback of the above processes is the requirement for a base or an acid to conduct the hydrolysis, as this necessitates a neutralization step. Further, in the majority of instances the intermediate product, namely, 4-hydroxy-3-quinolinecarboxylic acid, has to be isolated, making the process more complex.

U.S. Pat. No. 4,380,632 proposes improving the above process by carrying out the decarboxylation step via heat treatment, in the presence of an acidic catalyst such as sulfuric acid, phosphoric acid, or p-toluenesulfonic acid. The hydrolysis and decarboxylation reactions take place at the same time. The presence of an acidic catalyst nonetheless entails supplemental neutralization and purification steps to eliminate the catalyst.

SUMMARY OF THE INVENTION

A novel process has now been discovered that improves hydroxyquinoline preparation, while at the same time avoiding the above disadvantages and drawbacks to date characterizing the state of this art.

Briefly, the present invention features the preparation of the hydroxyquinolines by heating a 4-hydroxyquinolinecarboxylic acid ester in the presence of water but in the absence of a catalyst.

DETAILED DESCRIPTION OF BEST MODE AND SPECIFIC/PREFERRED EMBODIMENTS OF THE INVENTION

More particularly according to the present invention, it has now unexpectedly and surprisingly been determined that the hydrolysis and decarboxylation of 4-hydroxyquinolinecarboxylic acid esters can be carried out in very high reaction yields, in the absence of a catalyst, which has the advantage of greatly simplifying the process.

The present invention thus relates to quinolinic compounds.

By the term "quinolinic compound" is intended heterocyclic compound comprising a quinoline moiety. This term is also used for naphthpyridine type compounds that are also included in the scope of the process of the invention.

The heterocyclic ring member of the quinolinic compound is substituted by at least one hydroxyl group at the 4-position and an ester functional group at the position α to the hydroxyl group. Other substituents can also be present, in particular at the 5- and/or 7-position.

The starting material quinolinic compounds of the invention advantageously have the following structural formula (I):

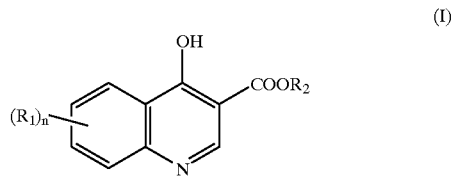

(I)

wherein the radicals $R_1$, which may be identical or different, are each a linear or branched alkyl radical having 1 to 12 carbon atoms, preferably 1 to 4 carbon atoms, such as methyl, ethyl, propyl, isopropyl, butyl, isobutyl, sec-butyl and tert-butyl radicals; a linear or branched alkyl radical substituted by one or more halogen atoms and having 1 to 6 carbon atoms, preferably 1 to 4 carbon atoms, such as halogenated methyl, ethyl, propyl, isopropyl, butyl, isobutyl, sec-butyl and tert-butyl radicals; a linear or branched alkenyl radical having 2 to 12 carbon atoms, preferably 2 to 4 carbon atoms, such as vinyl or allyl radicals; a cyclohexyl, phenyl or benzyl radical; a linear or branched alkoxy or thioether radical having 1 to 6 carbon atoms, preferably 1 to 4 carbon atoms, such as a methoxy, ethoxy, propoxy, isopropoxy or butoxy radical; an acyl radical having 2 to 6 carbon atoms; a nitro group; an amino group, optionally substituted by alkyl radicals having 1 to 6 carbon atoms; a halogen atom, preferably a chlorine or bromine atom; a trifluoromethyl radical; or an alkenylene radical having 3 or 4 carbon atoms and forming a ring member with the adjacent carbon atoms of the benzene moiety; $R_2$ is an alkyl radical having 1 to 12 carbon atoms, preferably 1 to 4 carbon atoms, such as methyl, ethyl, propyl, isopropyl, butyl, isobutyl, sec-butyl and tert-butyl radicals; a cycloalkyl radical having 5 or 6 carbon atoms, preferably a cyclohexyl radical; an aryl radical having 6 to 12 carbon atoms, preferably a phenyl radical; or an arylalkyl radical having 7 to 12 carbon atoms, preferably a benzyl radical; and n is a number ranging from 1 to 4, preferably 1 or 2.

Particularly suitable substituents at the 5- and/or 7-position are halogen atoms, such as fluorine, chlorine, bromine, iodine or a —$CF_3$ radical.

Preferred substituents $R_1$ are the chlorine atom, methyl radical and methoxy radical.

The chemical nature of $R_2$ is not critical provided that the carboxylate group is eliminated. For reasons of economy, it is usually a linear or branched alkyl radical having 1 to 12 carbon atoms, preferably 1 to 4 carbon atoms, but it is possible to employ other radicals, for example cyclohexyl, phenyl or benzyl radicals, or any other group.

Preferred compounds of formula (I) according to the process of the present invention are alkyl esters having 1 to 4 carbon atoms of 4-hydroxyquinolinecarboxylic acids.

Particularly representative are the alkyl esters of 4-hydroxy-7-chloroquinolinecarboxylic acid, 4-hydroxy-5-chloroquinolinecarboxylic acid and 4-hydroxy-5,7-dichloroquinolinecarboxylic acid.

Preferably, methyl or ethyl 4-hydroxy-5,7-dichloroquinoline-3-carboxylate are the starting materials of choice in the process of the invention.

The starting quinolinic compounds of formula (I) are known compounds that can, in particular, be prepared by reacting substituted anilines with alkyl alkoxymethylenemalonates (cf. C. C. Price et al., *Organic Synthesis*, 3, p. 272).

It should be appreciated that this invention is applicable to quinolinic compounds of formula (I) and also to the tautomeric forms thereof that can be represented by the structural formula (II):

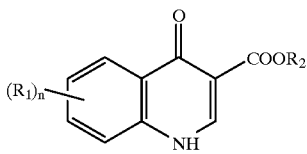
(II)

in which formula (II), $R_1$, $R_2$ and n have the definitions given above for formula (I).

According to the process of the invention, the hydrolysis step is carried out using water in either its liquid and/or vapor form.

The amount of water employed is preferably at least equal to the stoichiometric amount, more preferably in an excess amount which can be very large, for example 20 times the stoichiometric amount. Advantageously, the water is present in an excess of 5 to 15 times the stoichiometric amount.

Preferably, the water is added slowly during the reaction to limit entrainment of the organic liquid.

The decarboxylation is carried out either by heating the reaction mixture in the absence of any organic solvent to its melting point, or to a temperature slightly lower than its melting point in the event of decomposition of the starting material, or by heating in the presence of a heat exchange type organic liquid having a high boiling point.

The decarboxylation temperature is preferably 200° C. or more, more preferably in the range 200° C. to 250° C., and even more preferably in the range 230° C. to 240° C. A temperature above 250° C. can be employed depending on the nature of the organic liquid. It is about 270° C. when using a paraffin oil.

One organic liquid that is preferred for this type of reaction is a eutectic mixture of biphenyl oxide and biphenyl marketed under the trademarks THERMINOL VP1, DOWTHERM or GILOTHERM DO. When the organic liquid is indeed used, the decarboxylation temperature is advantageously selected such as to be in the preferred temperature zone.

Triphenylmethane, sulfolane, benzylbenzene, 1,4-dibenzylbenzene, a silicone oil, or petroleum cuts, having a high boiling point greater than the selected reaction temperature, can also be used.

From a practical standpoint, in general the quinolinic compound is introduced into the organic liquid indicated above in an amount, for example, of 10% to 50% by weight, preferably 10% to 30% by weight of the total weight of the reaction mixture, then heated slowly to the selected decarboxylation temperature (0.5° C. to 1° C. per minute). It is not necessary for all of the entire starting material to be dissolved in the reaction medium.

Water is slowly added at the selected reaction temperature.

Upon completion of the operation, a precipitate is recovered that essentially comprises the desired quinolinic compound (B) in equilibrium with its tautomeric form (A), having the following formulae:

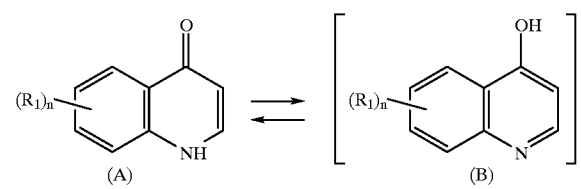

wherein $R_1$ and n are as defined above.

The precipitate is separated employing conventional solid/liquid separation techniques, preferably by filtering.

Washing the precipitate to eliminate trace amounts of organic liquid may be desirable. To this end, water or a solvent having a low boiling point, can be used, for example less than 150° C., preferably in the range 60° C. to 120° C. Particularly exemplary of eminently suitable solvents are o-dichlorobenzene, methylcyclohexane, benzene, toluene, chlorobenzene, methanol and ethanol.

The decarboxylated compound is obtained in a very high yield without the problem of neutralization and eliminating the catalyst.

The present invention is particularly well suited for the preparation of a 4-hydroxy-7-halogenoquinoline, preferably 4-hydroxy-7-chloroquinoline and isomer thereof, and a 4-hydroxy-5-halogenoquinoline, preferably 4-hydroxy-5-chloroquinoline. It is very well suited for preparing 5,7-dichloro-4-hydroxyquinoline.

In order to further illustrate the present invention and the advantages thereof, the following specific examples are given, it being understood that same are intended only as illustrative and in nowise limitative.

EXAMPLE 1

(a) Preparation of ethyl 4-hydroxy-5,7-dichloroquinoline-3-carboxylate:

210 ml of Therminol VP1 (solvent: eutectic mixture of biphenyl and biphenyl oxide), 27.8 g (0.129 mole) of ethyl ethoxymethylenemalonate and 20.65 g (0.125 mole) of 3,5-dichloroaniline were introduced into a stirred reactor provided with a distillation column and a water injection system and heated by an oil bath.

The mixture was heated from ambient temperature to 248° C. over 3 hours (h), then maintained at 248° C. for 1 h, 30 min; the ethanol formed was distilled off as it was formed.

(b) Hydrolysis/decarboxylation of the ethyl 4-hydroxy-5,7-dichloroquinoline-3-carboxylate thus Formed:

The temperature of the reaction mixture obtained in (a) was reduced to 230° C. and 10.4 g (0.58 mol) of water was continuously injected therein over 3 h, 20 min, by means of a tube at the level of the surface of the reaction mixture.

After cooling to ambient temperature, the 4-hydroxy-5,7-dichloroquinoline precipitate obtained was filtered, washed twice with 100 ml of o-dichlorobenzene, then dried.

Weight obtained: 22.5 g of 95.4% pure 4-hydroxy-5,7-dichloroquinoline (impurities: 3% of ethyl 4-hydroxy-5,7- dichloroquinoline-3-carboxylate, 0.4% of 4-hydroxy-5,7-dichloroquinoline-3-carboxylic acid, 0.1% of 4-hydroxy-7-chloroquinoline, 0.7% of Therminol VP1).

EXAMPLE 2

(a) Preparation of ethyl 4-hydroxy-5,7-dichloroquinoline-3-carboxylate:

A suspension of ethyl 4-hydroxyy-5,7-dichloroquinoline-3-carboxylate was prepared from 33.5 g (0.155 mole) of ethyl ethoxymethylene malonate, 24.3 g (0.15 mole) of 3,5-dichloroaniline and 263 g of Therminol VPI as described in Example 1.

(b) Hydrolysis/decarboxylation of the ethyl 4-hydroxy-5,7-dichloroquinoline-3-carboxylate thus Formed:

The temperature of the reaction mixture obtained in step (a) was reduced to 240° C.

10.4 g (0.58 mol) of water was continuously injected therein over 3 hours by means of a tube immersed in the reaction mixture.

After cooling to ambient temperature, the 4-hydroxy-5,7-dichloroquinoline precipitate obtained was filtered, washed twice with 100 ml of o-dichlorobenzene, then dried.

Weight obtained: 27.64 g of 98.3% pure 4-hydroxy-5,7-dichloroquinoline (impurities: 0.3% of ethyl 4-hydroxy-5,7-dichloroquinoline-3-carboxylate, 0. 1% of 4-hydroxy-5,7-dichloroquinoline-3-carboxylic acid, 0.2% of 4-hydroxy-7-chloroquinoline, 0.6% of Therminol VP 1).

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a 4-hydroxyquinoline and/or tautomer thereof, comprising heating and hydrolyzing/decarboxylating a 4-hydroxyquinolinecarboxylic acid ester in the presence of water, but in the absence of any catalyst therefor.

2. A process for the preparation of a 4-hydroxyquinoline and/or tautomer thereof, according to claim 1, comprising heating and hydrolyzing/decarboxylating a 4-hydroxyquinolinecarboxylic acid ester having the following structural formula (I):

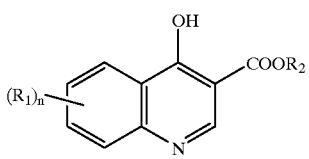

(I)

wherein the radicals $R_1$, which may be identical or different, are each a linear or branched alkyl radical having 1 to 12 carbon atoms; a linear or branched alkyl radical substituted by one or more halogen atoms and having 1 to 6 carbon atoms; a linear or branched alkenyl radical having 2 to 12 carbon atoms; a cyclohexyl, phenyl or benzyl radical; a linear or branched alkoxy or thioether radical having 1 to 6 carbon atoms; an acyl radical having 2 to 6 carbon atoms; a nitro group; an amino group, optionally substituted by alkyl radicals having 1 to 6 carbon atoms; a halogen atom; a trifluoromethyl radical; or an alkenylene radical having 3 or 4 carbon atoms and forming a ring member with the adjacent carbon atoms of the benzene moiety; $R_2$ is an alkyl radical having 1 to 12 carbon atoms; a cycloalkyl radical having 5 or 6 carbon atoms; an aryl radical having 6 to 12 carbon atoms; or an arylalkyl radical having 7 to 12 carbon atoms; and n is a number ranging from 1 to 4.

3. A process for the preparation of a 4-hydroxyquinoline and/or tautomer thereof, according to claim 1, comprising heating and hydrolyzing/decarboxylating a 4-hydroxyquinolinecarboxylic acid ester having the following structural formula (I'):

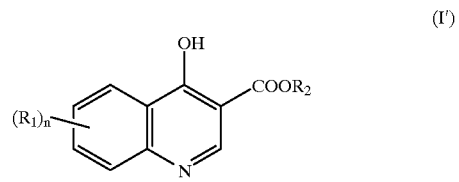

(I')

wherein the radicals $R_1$, which may be identical or different, are each a linear or branched alkyl radical having 1 to 4 carbon atoms; a linear or branched alkyl radical substituted by one or more halogen atoms and having 1 to 4 carbon atoms; a linear or branched alkenyl radical having 2 to 4 carbon atoms; a cyclohexyl, phenyl or benzyl radical; a linear or branched alkoxy or thioether radical having 1 to 4 carbon atoms; an acyl radical having 2 to 6 carbon atoms; a nitro group; an amino group, optionally substituted by alkyl radicals having 1 to 6 carbon atoms; a halogen atom; a trifluoromethyl radical; or an alkenylene radical having 3 or 4 carbon atoms and forming a ring member with the adjacent carbon atoms of the benzene moiety; $R_2$ is an alkyl radical having 1 to 4 carbon atoms; a cycloalkyl radical having 5 or 6 carbon atoms; an aryl radical having 6 to 12 carbon atoms; or an arylalkyl radical having 7 to 12 carbon atoms; and n is 1 or 2.

4. The process as defined by claim 2, wherein formula (I), the radicals $R_1$, which may be identical or different, are each a chlorine atom, a methyl radical, or a methoxy radical.

5. The process as defined by claim 2, wherein formula (I), $R_2$ is an alkyl radical having from 1 to 6 carbon atoms.

6. The process as defined by claim 1, comprising heating and hydrolyzing/decarboxylating a $C_1$–$C_4$ alkyl ester of a 4-hydroxyquinolinecarboxylic acid.

7. The process as defined by claim 2, said starting material 4-hydroxyquinolinecarboxylic acid ester comprising the tautomer thereof having the following structural formula (II):

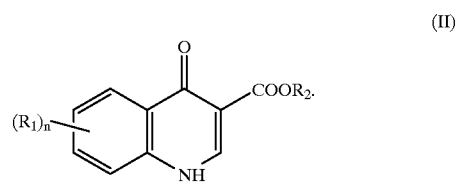

(II)

8. The process as defined by claim 2, said starting material 4-hydroxyquinolinecarboxylic acid ester (I) comprising an alkyl ester of 4-hydroxy-7-chloroquinolinecarboxylic acid, of 4-hydroxy-5-chloroquinolinecarboxylic acid, or of 4-hydroxy-5,7-dichloroquinolinecarboxylic acid.

9. The process as defined by claim 8, said starting material 4-hydroxyquinolinecarboxylic acid ester (I) comprising methyl or ethyl 4-hydroxy-5,7-dichloroquinoline-3-carboxylate.

10. The process as defined by claim 1, carried out in the presence of liquid water.

11. The process as defined by claim 1, carried out in the presence of water vapor.

12. The process as defined by claim 1, carried out in the presence of an at least stoichiometric amount of water.

13. The process as defined by claim 12, carried out in the presence of an amount of water at least 5 times greater than the stoichiometric amount.

14. The process as defined by claim 1, carried out by heating and hydrolyzing/decarboxylating said 4-hydroxyquinolinecarboxylic acid ester in an organic liquid.

15. The process as defined by claim 14, said organic liquid comprising a paraffin oil, a eutectic mixture of biphenyl oxide and biphenyl, triphenylmethane, sulfolane, benzylbenzene, 1,4-dibenzylbenzene, a silicone oil, or a petroleum cut.

16. The process as defined by claim 14, comprising introducing said 4-hydroxyquinolinecarboxylic acid ester into said organic liquid in such amount as to constitute from 10% to 50% by weight of the reaction medium thus formed and then slowly heating said reaction medium to the decarboxylation temperature of said 4-hydroxyquinolinecarboxylic acid ester.

17. The process as defined by claim 16, comprising slowly adding the water to said medium of reaction.

18. The process as defined by claim 1, carried out at a decarboxylation temperature of at least 200° C.

19. The process as defined by claim 18, carried out at a decarboxylation temperature of from 200° C. to 250° C.

20. The process as defined by claim 19, carried out at a decarboxylation temperature of from 230° C. to 240° C.

* * * * *